(12) United States Patent
Sakai et al.

(10) Patent No.: US 11,685,884 B2
(45) Date of Patent: Jun. 27, 2023

(54) DEVICE, METHOD AND PROGRAM FOR IDENTIFICATION OF PROJECTION TARGETS

(71) Applicant: Tamagawa Academy & University, Tokyo (JP)

(72) Inventors: Yutaka Sakai, Tokyo (JP); Yoshikazu Isomura, Tokyo (JP)

(73) Assignee: Tamagawa Academy & University, Tokyo (JP)

( * ) Notice: Subject to any disclaimer, the term of this patent is extended or adjusted under 35 U.S.C. 154(b) by 722 days.

(21) Appl. No.: 16/633,511

(22) PCT Filed: Dec. 13, 2017

(86) PCT No.: PCT/JP2017/044696
§ 371 (c)(1),
(2) Date: Jan. 23, 2020

(87) PCT Pub. No.: WO2019/021505
PCT Pub. Date: Jan. 31, 2019

(65) Prior Publication Data
US 2021/0009930 A1 Jan. 14, 2021

(30) Foreign Application Priority Data
Jul. 28, 2017 (JP) .............................. JP2017-146456

(51) Int. Cl.
*C12M 1/34* (2006.01)
*A61N 5/06* (2006.01)
(Continued)

(52) U.S. Cl.
CPC ................ *C12M 1/34* (2013.01); *A61B 5/00* (2013.01); *A61B 5/0042* (2013.01);
(Continued)

(58) Field of Classification Search
CPC ....... A61B 5/00; A61B 5/0042; A61B 5/0059; A61B 5/311; A61B 5/388; A61B 5/4041;
(Continued)

(56) References Cited

FOREIGN PATENT DOCUMENTS

JP 2015-208308 A 11/2015

OTHER PUBLICATIONS

International Search Report issued in PCT/JP2017/044696; dated Mar. 20, 2018.
(Continued)

*Primary Examiner* — Mark D Remaly
(74) *Attorney, Agent, or Firm* — Studebaker & Brackett PC

(57) ABSTRACT

The purpose of the present invention is to provide a technique whereby multiple projection targets are efficiently identified from multiple neurons in multiple brain areas with the use of multis-point light stimulation. An acquisition unit 52 acquires spike signals generated from multiple neurons existing in the vicinity of two or more recording sites. A stimulation control unit 51 selects one projection target candidate from two or more candidates in accordance with a definite system on the basis of the spike signals and then determines irradiation timing of light stimulation. Upon the light stimulation, a management unit 53 acquires the spike signals in all of the recording sites within a definite period of time before or after the light stimulation, while dividing the spike signals into anti responses and collision responses. An anti response management unit 81 acquires and manages information relating to the anti responses. A collision response management unit 82 acquires and manages information relating to the collision responses. A priority control section 54 corrects and determines priority depending on the anti response information and the collision response information.

3 Claims, 7 Drawing Sheets

(51) Int. Cl.
*C12N 5/0793* (2010.01)
*A61B 5/00* (2006.01)
*A61B 5/311* (2021.01)
*A61B 5/388* (2021.01)

(52) U.S. Cl.
CPC ............ *A61B 5/0059* (2013.01); *A61B 5/311* (2021.01); *A61B 5/388* (2021.01); *A61B 5/4041* (2013.01); *A61B 5/4094* (2013.01); *A61N 5/0622* (2013.01); *C12N 5/0619* (2013.01)

(58) Field of Classification Search
CPC ................ A61B 5/4088; A61B 5/4094; A61N 2005/0626; A61N 2005/0662; A61N 5/0622; C12M 1/34; C12N 5/0619
See application file for complete search history.

(56) References Cited

OTHER PUBLICATIONS

Akiko Saiki, et al.; "In Vivo Spiking Dynamics of Intra- and Extratelencephalic Projection Neurons in Rat Motor Cortex"; Cerebral Cortex; Jan. 31, 2017; vol. 28, No. 3; pp. 1024-1038, 1026, Lower right column, second paragraph, to p. 102, left column, second paragraph, p. 1029 left column, the last paragraph, to right column, second paragraph, fig. 1.

DEVICE, METHOD AND PROGRAM FOR IDENTIFICATION OF PROJECTION TARGETS

TECHNICAL FIELD

The present invention relates to a projection target identification device, a projection target identification method, and a program.

BACKGROUND ART

In the related art, diseases of nervous systems such as epilepsy and Alzheimer disease are known as diseases difficult to treat, and elucidation of disease states thereof is strongly desired. In this regard, as one of basic research aimed at elucidating the diseases of the nervous systems, development of a technology for identifying projection targets of neurons has been suggested (for example, Patent Document 1). According to a technology described in Patent Document 1, the function of shifting in a transsynaptic retrograde manner is imparted to a site-specific DNA recombination enzyme and is introduced into neurons, thereby identifying the projection targets of the neurons and the like.

Patent Document 1: Japanese Unexamined Patent Application, Publication No. 2015-208308

DISCLOSURE OF THE INVENTION

Problems to be Solved by the Invention

However, in the related art which includes the technology described in Patent Document 1, only a single projection target can be identified, and it is pointed out that the technologies are insufficient for efficiently identifying a plurality of projection targets from a plurality of neurons which exist nearby. In addition, with regard to the technology described in Patent Document 1, it is pointed out that the technology is not configured to detect a functional spike signal in a unit of millisecond which is transmitted and received by a neuron, and thus it is difficult to elucidate how the projection functions even when the projection target is identified.

The invention has been made in consideration of such circumstances, and an object thereof is to efficiently identify a plurality of projection targets from a plurality of neurons in a plurality of brain areas by using a multi-point spike signal record and multi-point stimulation, and to realize analysis of a spike signal of the neurons which are identified.

Means for Solving the Problems

To accomplish the above-described object, according to an aspect of the invention, there is provided a neuron projection target identification device that identifies one or more projection targets among K pieces (K is an integral value of two or greater) of projection target candidates (for example, stimulation sites S-1 to S-K in FIG. 4) with respect to predetermined projection source cells (for example, recording cells N1 to N3 in FIG. 4). The projection target identification device includes:
a spike signal acquisition unit that records spike signals of a plurality of neurons at L pieces (L is an integral value of two or greater) of recording sites (R-1 to R-L) on the basis of a predetermined system;
a stimulation timing determination unit that determines a timing of applying stimulation to the projection target candidates on the basis of spike signal information;
a projection target determination unit that determines whether or not the projection target candidates are real projection targets on the basis of the spike signal information within a predetermined period of time before or after the stimulation when the stimulation is applied to the projection target candidates; and
a priority control unit that corrects a method of the stimulation timing determination on the basis of a determination result of the projection target determination unit and the spike signal information.

A neuron projection target identification method and a program according to other aspects of the invention are provided as a method and a program which correspond to the neuron projection target identification device according to the aspect of the invention.

Effects of the Invention

According to the invention, it is possible to efficiently identify a plurality of projection targets from a plurality of neurons in a plurality of brain areas by using a multi-point spike signal record and multi-point stimulation.

PREFERRED MODE FOR CARRYING OUT THE INVENTION

Figure 1:
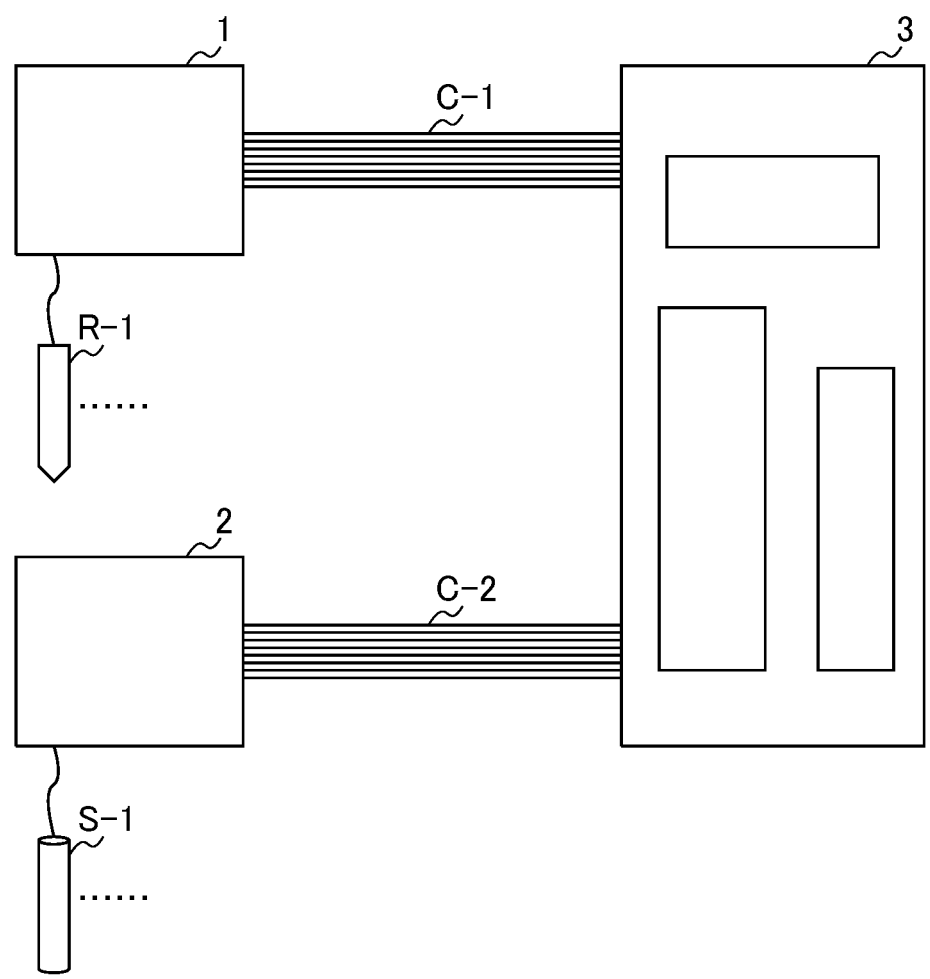
FIG. 1 is a block diagram illustrating an example of a configuration of an information processing system according to an embodiment of the invention.

Here, with regard to description relating to one embodiment of the invention, a technology that is a premise will be briefly described.
(1) Multi-Channel Recording and Spike Sorting Technology
A multi-channel recording and spike sorting technology is a technology of sorting spike signals derived from neurons by using a detection intensity difference between a plurality of electrodes on the basis of the principle of stereo microphone. Typically, four-channel recording waveforms are acquired, and clustering is executed in a four-channel pattern space. Only with the multi-channel recording and spike sorting technology, it is possible to sort out a neuron that is a generation source of a spike signal, but there is a problem that it is difficult to understand a projection target of each cell.

(2) Spike Collision Identification Method

In a spike collision identification method, a retrograde (a direction opposite to an original spike signal flow) spike is detected by electrically stimulating projection targets of neurons. In addition, in the spike collision identification method, a spike that spontaneously occurs is detected, and a projection target is stimulated in advance to confirm that a retrograde spike and an anterograde spike collide with each other in the middle and disappear, and it is confirmed that a projection source neuron and a position of the projection target are directly connected in a reliable manner. With regard to the spike collision identification method, it is pointed out that a probability of matching between the projection source neuron and the position of the projection target is low, and thus identification efficiency of the projection target is poor.

(3) Identification Method Using Gene Modification Technology

An identification method using gene-modified virus infection is an identification technology of injecting a virus incorporated with a gene exhibiting a functional molecule capable of identifying a cell at a recording site for infection into a projection target in a retrograde manner. The technology is also realized by using a gene-modified animal in which a similar functional molecule is exhibited in advance. Note that, the functional molecule to be exhibited is not particularly limited. For example, Channelrhodopsin (ChR2) that is used often as optogenetics is employed. In this case, it is possible to easily cause a spike to occur in a neuron through irradiation with blue light, and it is possible to record a spike signal while identifying a projection target by simultaneously performing the irradiation with the blue light and a spike signal record. It is principally possible to identify a plurality of projection targets by using functional molecules of which optical wavelengths to be excited are different from each other, but it is pointed out that identification of the plurality of projection targets is difficult due to a limitation of an optical wavelength band. A projection target identification device according to an embodiment of the invention can efficiently identify the plurality of projection targets from a plurality of neurons by appropriately using and applying the premise technologies.

Next, meanings of technical terminologies used in the embodiment of the invention will be briefly described. Meanings of technical terminologies used in this embodiment are as follows. Description will be made later by appropriately using the terminologies. An anterograde spike is a spike that occurs from a cell body of a neuron, and an electric signal is transmitted to a projection target thereof. That is, a spike that spontaneously occurs is the anterograde spike. A retrograde spike is a spike that occurs by stimulating the projection target, and is transmitted to a cell body in a direction opposite to a typical case. A recording site is a location at which a spike that occurs in a cell body of a neuron is recorded. Even in the same brain area, a plurality of the recording sites are assumed. However, in this embodiment, a tetrode electrode including a set of four channels is assumed, but a method of application of the present technology does not matter as long as a spike of a cell body can be recorded. A stimulation site is a location that is stimulated. If a spike of a neuron which is projected to the stimulation site can be recorded at any of the recording sites, it is possible to make a record for projection target identification. Even in the same brain area, a plurality of the stimulation sites are assumed. In this embodiment, light stimulation by optogenetics is assumed, but a method thereof does not matter as long as the retrograde spike can be caused to occur. A tetrode is an electrode including a set of four channels. It is possible to determine that a spike occurs from any nearby neuron on the basis of the principle of stereo microphone. A stimulation response is a four-channel potential waveform of any recording site which is obtained by stimulating any stimulation site. It is difficult to understand whether or not a spike included in the stimulation response is the retrograde spike. Among stimulation responses, a response that satisfies a condition of an anti response or a collision response is referred to as an anti response or a collision response. The anti response is a stimulation response when a spontaneous spike does not occur in a constant period before stimulation. The anti response represents a stimulation response without a possibility of collision with the anterograde spike, and is a response for reliably observing a retrograde spike in a case where the retrograde spike exists. An anti candidate spike is a spike that is observed with good reproducibility in the anti response. A collision response is a stimulation response when only a piece of spontaneous spike occurs in a constant period before stimulation. A case where the spontaneous spike is transmitted in an anterograde manner, collision occurs, and the anti candidate spike shown in the anti response disappears is referred to as "collision success response", and a case where the anti candidate spike does not disappear is referred to as "collision failure response". The responses are responses for making a determination as to whether a spike is the retrograde spike. A target spike is a spontaneous spike that is set as a target for taking the collision response. When only the target spike occurs in a constant period, the collision response can be obtained by performing stimulation. In this embodiment, a projection target identification device 3 identifies one or more projection targets among K pieces (K is an integral value of two or greater) of projection target candidates (for example, stimulation sites S-1 and S-2 in FIG. 4) with respect to predetermined projection source cells (for example, recording cells N1, N2, and N3 in FIG. 4).

Hereinafter, an embodiment of the invention will be described with reference to the accompanying drawings. FIG. 1 is a configuration diagram illustrating an example of a configuration of an information processing system to which the invention is applied.

An information processing system illustrated in FIG. 1 includes a multi-cell recording device 1, a multi-point light stimulation device 2, and a projection target identification device 3. Here, the multi-cell recording device 1 and the multi-point light stimulation device 2 are respectively connected to the projection target identification device 3 through parallel cables C-1 and C-2. Note that, the parallel cables C-1 and C-2 are not essential constituent elements, and communication may be performed by short range radio communication such as Blue Tooth (registered trademark) in addition to wired communication such as a serial cable.

The multi-cell recording device 1 includes a device that records spike signals which are generated in a plurality of nearby neurons at a plurality of recording sites R-1 to R-L (L is an arbitrary integral value of two or greater). The multi-point light stimulation device 2 includes a light stimulation device at a plurality of stimulation sites S-1 to S-K (K is an arbitrary integral value of two or greater). Note that, the multi-cell recording device 1 transmits information (hereinafter, referred to as "cell record information") such as an electric signal relating to a spike signal that is measured to the projection target identification device 3.

The multi-point light stimulation device 2 is a light irradiation device capable of performing irradiation with specific wavelength light (for example, blue light). Here, in this embodiment, as a gene-modified animal that is used in an experiment, a rat in which ChR2 is exhibited at the entirety of the brain is employed (for example, refer to the related art "(3) Identification method using gene-modified virus infection"). That is, the multi-point light stimulation device 2 can artificially cause a spike to occur by irradiating an arbitrary neuron with blue light.

For example, the multi-cell recording device 1 is a multi-point electrode (a silicon probe or the like), and can measure spike signals of a plurality of neurons. Here, the multi-cell recording device 1 and the multi-point light stimulation device 2 can be used in combination through the projection target identification device 3. That is, since the devices are used in combination, it is possible to perform combinational analysis of a plurality of light stimulations and a plurality of recording sites. As a result, it is possible to effectively and simultaneously identify spike signals which are transmitted between a plurality of brain areas (for example, refer to related art "multi-channel recording and spike sorting technology" and "(2) spike collision identification method").

Figure 2:
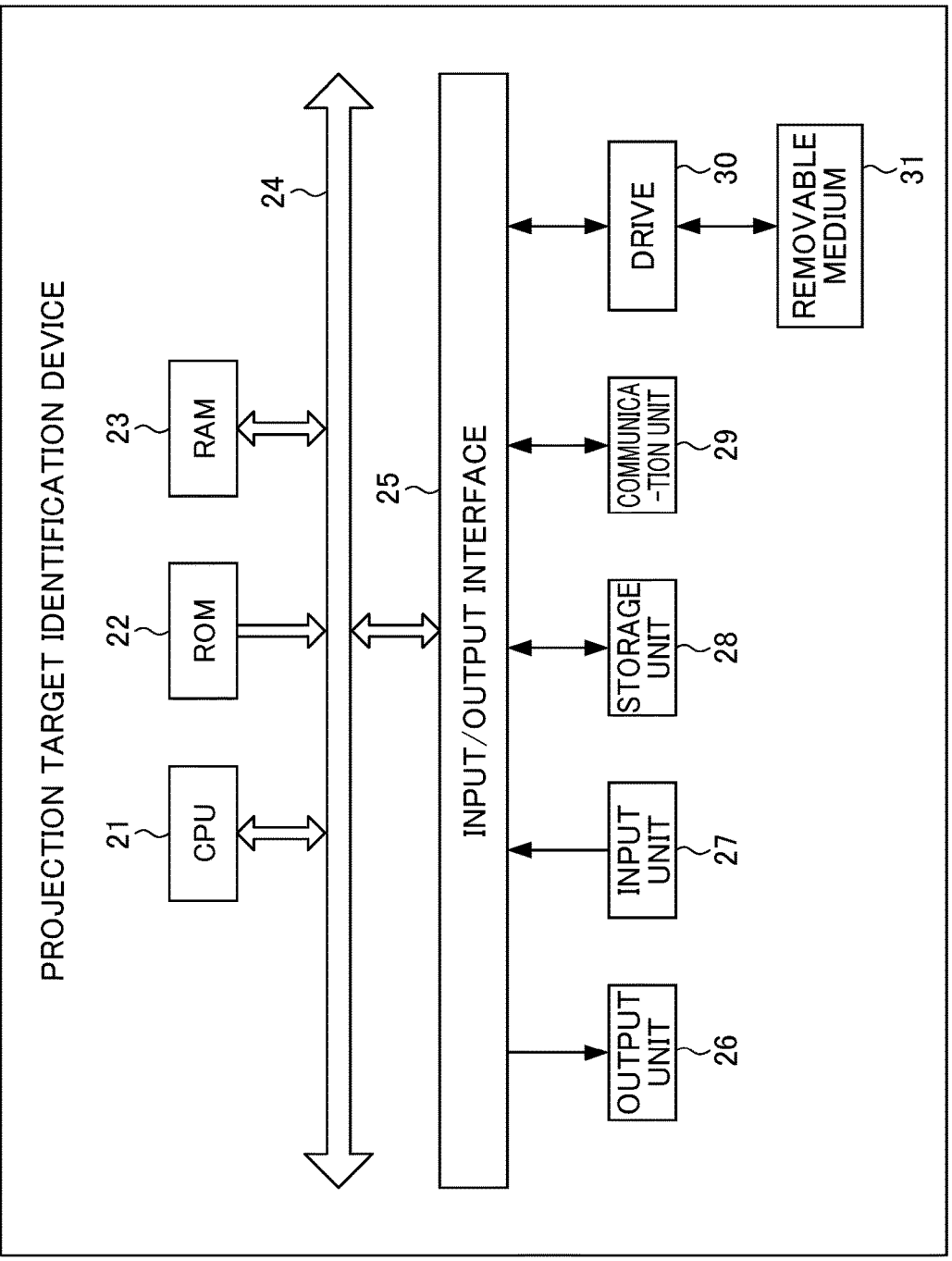
FIG. 2 is a block diagram illustrating an example of a hardware configuration in a projection target identification device in the information processing system illustrated in FIG. 1.

Next, a hardware configuration of the projection target identification device 3 will be described. FIG. 2 is a block diagram illustrating an example of the hardware configuration of the projection target identification device 3 in the information processing system illustrated in FIG. 1.

The projection target identification device 3 includes a central processing unit (CPU) 21, a read only memory (ROM) 22, a random access memory (RAM) 23, a bus 24, an input/output interface 25, an output unit 26, an input unit 27, a storage unit 28, a communication unit 29, and a drive 30.

The CPU 21 executes various processes in accordance with a program stored in the ROM 22 or a program loaded from the storage unit 28 to the RAM 23. Data that is necessary when the CPU 21 executes various processes is also appropriately stored in the RAM 23.

The CPU 21, the ROM 22, and the RAM 23 are connected to each other through the bus 24. The input/output interface 25 is also connected to the bus 24. The output unit 26, the input unit 27, the storage unit 28, the communication unit 29, and the drive 30 are connected to the input/output interface 25.

The output unit 26 is constituted by a display, a printer, a speaker, or the like, and outputs various pieces of information as an image, a printed matter, or a voice. For example, in this embodiment, a result indicating projection targets of respective neurons which are identified is displayed on a display or the like. The input unit 27 is constituted by a keyboard, a mouse, a touch panel, or the like, and inputs various pieces of information.

The storage unit 28 is constituted by a hard disk, a dynamic random access memory (DRAM), or the like, and stores various pieces of data. The communication unit 29 controls communication that is performed with another terminal through a network or the like. For example, in this embodiment, communication performed with the multi-cell recording device 1 or the multi-point light stimulation device 2 through the parallel cable C-1 or C-2 (FIG. 1) is controlled.

A removable medium 31 constituted by a magnetic disk, an optical disc, a magneto-optical disk, a semiconductor memory, or the like is appropriately mounted to the drive 30. A program that is read out from the removable medium 31 by the drive 30 is installed in the storage unit 28 as necessary. In addition, as in the storage unit 28, the removable medium 31 can also store various pieces of data stored in the storage unit 28.

The projection target identification device 3 having the above-described hardware configuration has the following functional configuration when executing a projection target identification process to be described later. Here, a functional configuration of the projection target identification device 3 will be described. Note that, the projection target identification process represents a series of processes of repeating a process of measuring light stimulation to a stimulation site that becomes a projection target candidate and responses (spike signals) of all recording sites with respect to the light stimulation and determining a stimulation site to which the subsequent light stimulation is applied and a timing from a result of the measurement, and efficiently identifying a plurality of projection targets of a plurality of neurons.

Figure 3:
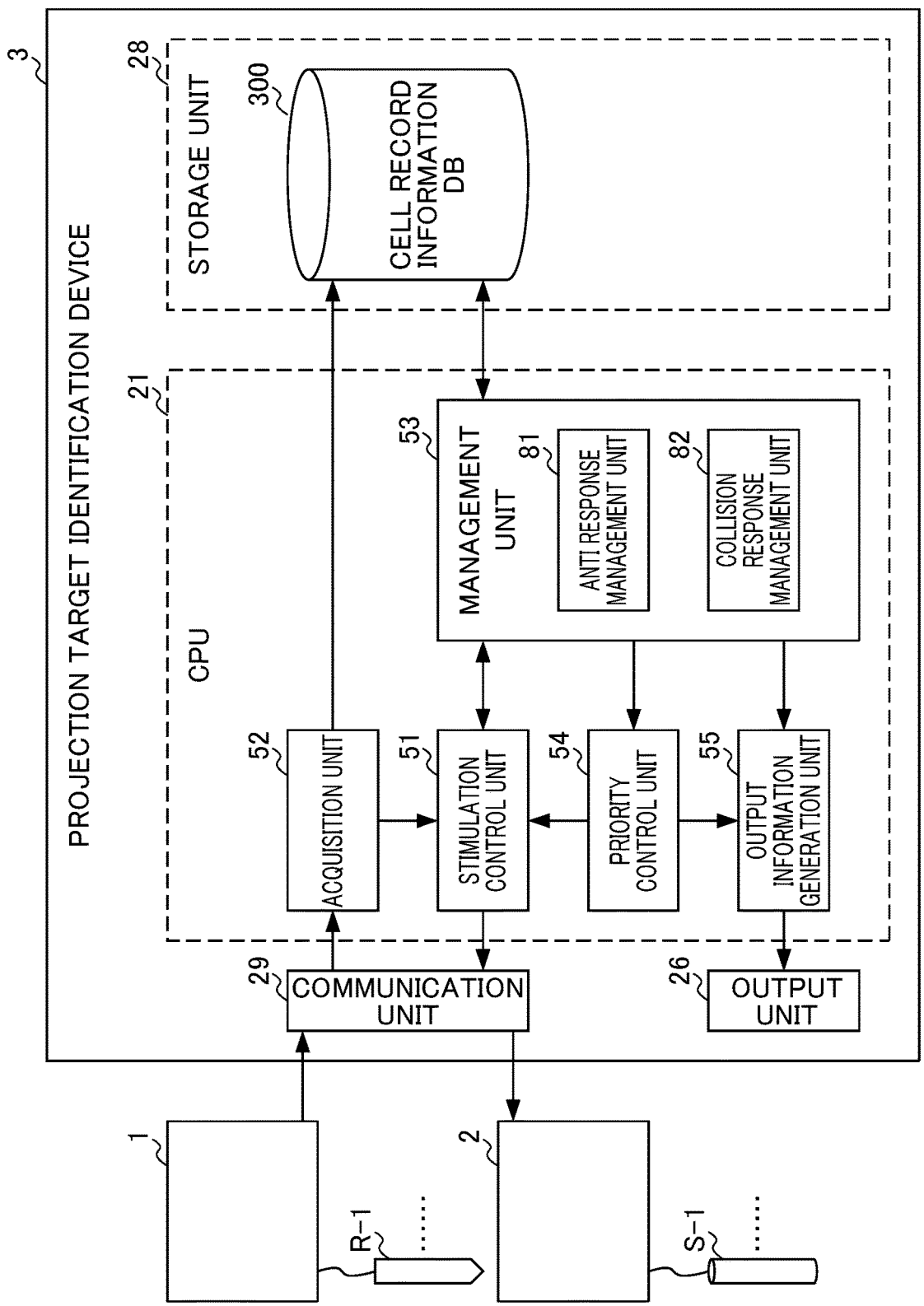
FIG. 3 is a functional block diagram illustrating an example of a functional configuration of the projection target identification device illustrated in FIG. 2.

FIG. 3 is a functional block diagram illustrating an example of a functional configuration of the projection target identification device 3 illustrated in FIG. 2. In the CPU 21 of the projection target identification device 3, a stimulation control unit 51, an acquisition unit 52, a management unit 53, a priority control unit 54, and an output information generation unit 55 function.

The stimulation control unit 51 determines irradiation timing of light stimulation that is applied to K pieces (K is an integral value of two or greater) of projection target candidates on the basis of a predetermined system. In addition, the stimulation control unit 51 receives constant-period cell record information that is recorded at all of the recording sites from the acquisition unit 52, and calculates the priority of each of the stimulation sites for every time. A command for applying light stimulation to an arbitrary stimulation site is transmitted to the multi-point light stimulation device 2 at timing exceeding constant priority at the arbitrary stimulation site. In addition, the stimulation control unit 51 appropriately receives control relating to the priority from the priority control unit 54 to be described later. A method relating to priority control by the priority control unit 54 will be described with reference to FIG. 4 and the subsequent drawings.

The acquisition unit 52 stores cell record information for a constant period in the past while acquiring and updating cell record information of all of the recording sites for every time, and transmits the cell record information to the stimulation control unit 51. In addition, in a case where light stimulation is applied, the acquisition unit 52 stores cell record information of the all recording sites within a predetermined period of time before or after the light stimulation to a cell record information DB 300.

The management unit 53 is provided with an anti response management unit 81 and a collision response management unit 82. In a case where the anti response is recorded in the priority determined by the stimulation control unit 51 and the cell record information acquired from the cell record information DB 300, the anti response management unit 81 acquires and manages information relating to the anti response (hereinafter, referred to "anti response information"). Specifically, in a case where a response, which is a stimulation response without possibility of collision with the anterograde spike and is a response for reliably observing a retrograde spike in a case where the retrograde spike exists, is recorded in the cell record information, the information is acquired and managed. In a case where the collision response is recorded in the cell record information acquired from the cell record information DB 300, the collision response management unit 82 acquires and manages information relating to the collision response (hereinafter, referred to as "collision response information"). Specifically, in a case where a response for determining whether or not a spike is the retrograde spike on the basis of whether or not a spontaneous spike is transmitted in an anterograde manner, collision occurs, and the anti candidate spike shown in the anti response disappears is recorded in the cell record information, the information is acquired and managed. Note that, each of the anti response management unit 81 and the collision response management unit 82 transmits information to be output to the output information generation unit 55.

The priority control unit 54 executes control of correcting and determining priority on the basis of at least one of the cell record information and a result determined by a response determination unit (for example, the anti response information and the collision response information). That is, the priority control unit 54 executes control of correcting and determining the priority on the basis of at least one piece of information between information relating to the anti response managed by the anti response management unit 81 and information relating to the collision response managed by the collision response management unit 82.

The output information generation unit 55 executes control of generating various pieces of information (for example, information relating to a projection source of an identified neuron and a projection target of a neuron, or the like) output to a display or the like of the output unit 26. Next, detailed functions of the stimulation control unit 51, the acquisition unit 52, the anti response management unit 81, the collision response management unit 82, and the like described above will be described in detail with reference to FIG. 4 and FIG. 5.

Figure 4:
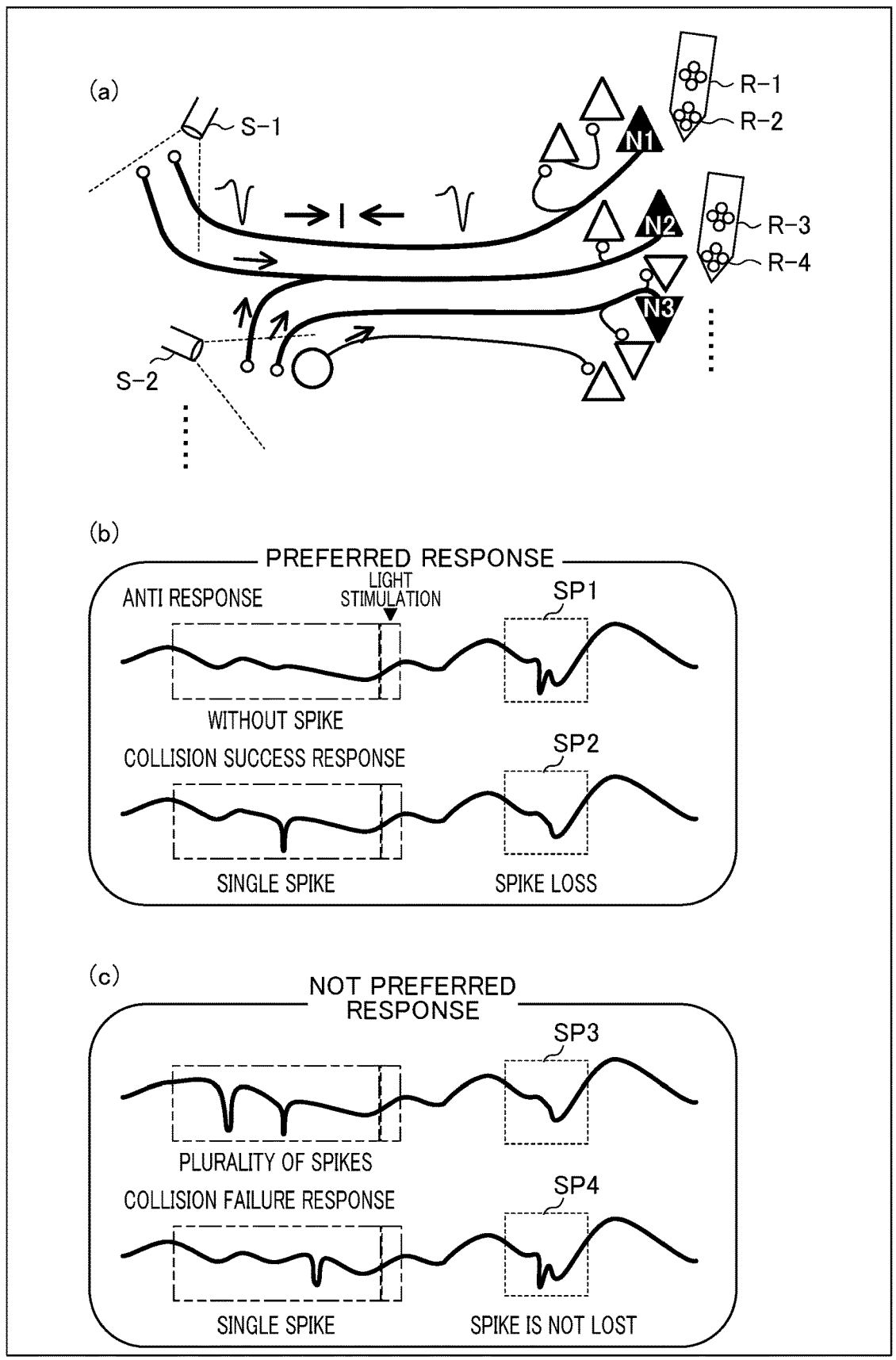
FIG. 4 is a diagram illustrating an example of a drawing for optimizing efficiency per stimulation performed once.

FIG. 4 is a diagram illustrating an example of a drawing for optimizing efficiency per stimulation performed once. In FIG. 4(a), for example, an example in which the stimulation sites S-1 and S-2 are stimulated, and cell record information is acquired at recording sites R-1 to R-4 is illustrated. In the example illustrated in FIG. 4(a), the multi-point light stimulation device 2 applies light stimulation to a plurality of the stimulation sites S-1 and S-2. In contrast, the multi-cell recording device 1 acquires the cell record information at a plurality of the recording sites R-1 to R-4. Note that, it is not necessary to set only one stimulation site to one brain area, and a plurality of stimulation sites can be set. In addition, similarly, a plurality of the recording sites can be set in the one brain area.

Here, in this embodiment, as a method of identifying the projection target of the neuron, the above-described "(2) spike collision identification method" may be employed. That is, as described in the related art "(2) spike collision identification method", retrograde spikes which occur due to electric stimulation to the stimulation sites S-1 to S-K are detected at the recording sites R-1 to R-L. In addition, a spike that spontaneously occurs is detected, and a stimulation site is stimulated in advance to confirm that a retrograde spike and an anterograde spike collide with each other in the middle and disappear, and it is confirmed that a projection source neuron and a position of the projection target are directly connected in a reliable manner. Note that, in this embodiment, it is possible to execute wide-range light stimulation at a plurality of stimulation sites without applying a damage to a nervous system differently from electric stimulation that can be used in "(2) spike collision identification" in the related art. In addition, in this embodiment, it is possible to acquire the cell record information simultaneously at a plurality of recording sites. Accordingly, in this embodiment, it is possible to efficiently identify a plurality of projection targets of a plurality of neurons.

Details of the cell record information obtained at an arbitrary channel of an arbitrary recording site (R-2 in FIG. 4) before and after light stimulation of an arbitrary stimulation site (S-1 in FIG. 4) are illustrated in FIG. 4(b) and FIG. 4(c). An upper drawing in FIG. 4(b) illustrates a waveform of a typical anti response. That is, in a case where a spontaneous spike does not occur, a retrograde spike that occurs by stimulating a stimulation site is observed as is (refer to SP1). On the other hand, a lower drawing in FIG. 4(b) represents a typical collision success response. That is, since the spontaneous spike is transmitted in an anterograde manner, the spontaneous spike collides with the retrograde spike that occurs due to stimulation to the stimulation site, and loss of the anti candidate spike that is seen in the anti response is observed (refer to SP2). In summary, in a case where only one piece of spike, which spontaneously occurs at the recording site R-2, is detected in a constant period, and a collision success response is confirmed by applying stimulation to the stimulation site S-1 in advance, it is possible to confirm that a neuron that emits the spontaneous spike is directly projected to the stimulation site S-1. On the other hand, a lower drawing in FIG. 4(c) represents a typical collision failure response. When loss of the anti candidate spike that is seen in the anti response is not confirmed (refer to SP4), it is possible to confirm that the neuron that emits the spontaneous spike is not directly connected to the stimulation site S-1. However, as in an upper drawing in FIG. 4(c), in a case where spikes spontaneously occur from a plurality of neurons in a constant period, even when loss of the anti candidate spike is confirmed by stimulating the stimulation site in advance (refer to SP3), it is difficult to understand that the loss is caused by which spontaneous spike. Accordingly, in a case where the plurality of spontaneous spikes occur, it is necessary to avoid light stimulation.

Figure 5:
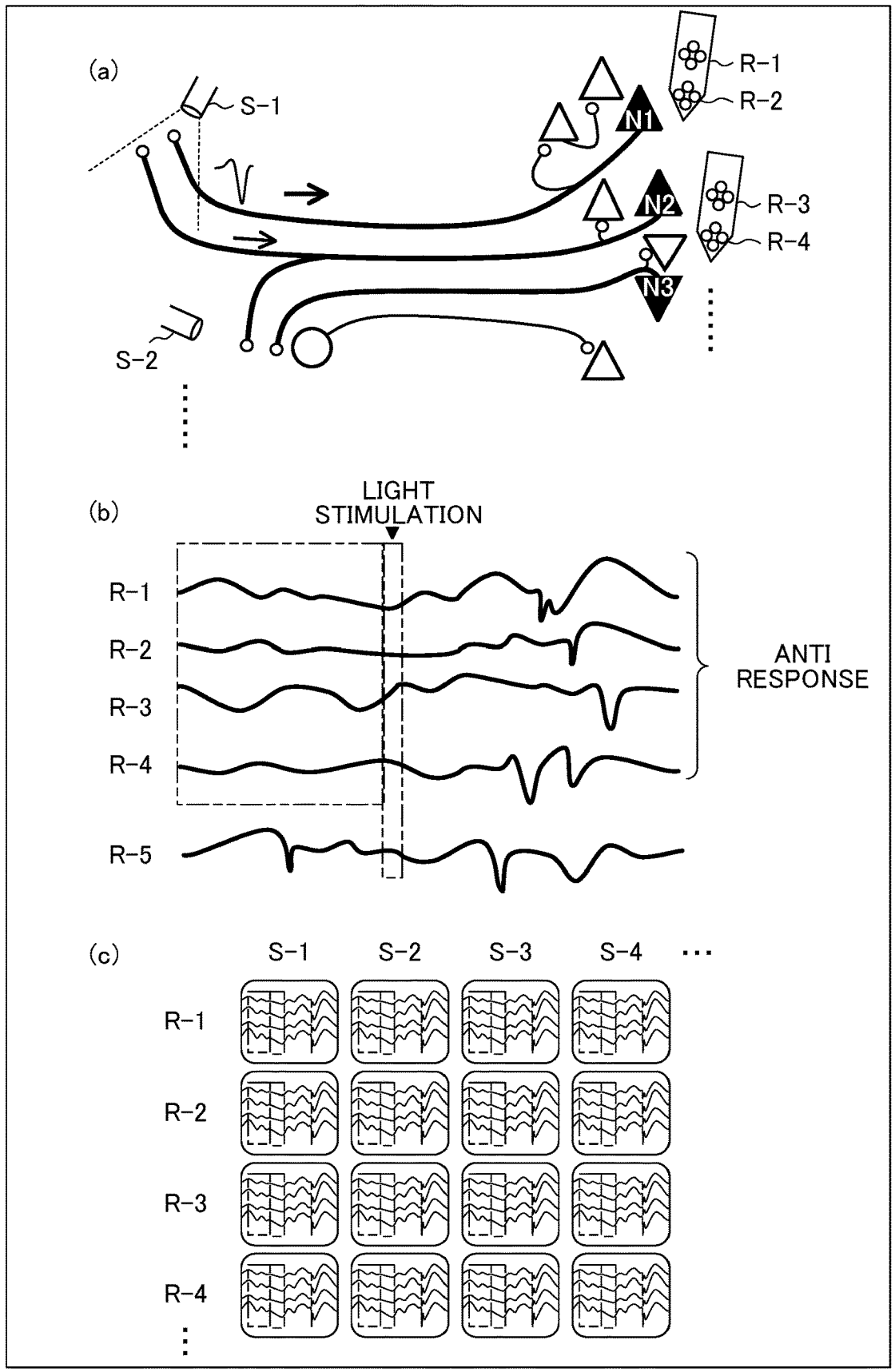
FIG. 5 is a diagram illustrating an example of a drawing relating to efficient anti response acquisition.

Next, FIG. 5 is a diagram illustrating an example of a drawing relating to efficient anti response acquisition. For example, FIG. 5(a) illustrates an example in which cell record information is acquired at all recording sites R-1 to R-L by stimulating an arbitrary stimulation site S-1.

Here, as an example, FIG. 5(b) illustrates an example of the cell record information acquired at recording sites R-1 to R-5. Note that, in the drawing, a portion corresponding to only one channel of a four-channel recording waveform is displayed. In the example in FIG. 5(b), a spike signal is not generated in the recording sites R-1 to R-4 for a constant period. The timing is detected by the stimulation control unit 51, and light stimulation is applied to a projection target candidate to acquire anti responses at four recording sites at a time. As described above, it is possible to efficiently acquire the anti responses by applying the light stimulation at timing at which the spike signal is not generated for a constant period at as many recording sites as possible. Note that, data that is acquired is stored in the cell record information DB 300, and is managed by the anti response management unit 81.

Here, FIG. 5(c) is a diagram illustrating that anti responses are efficiently acquired in a combination of each stimulation site and each recording site.

The anti response management unit 81 acquires anti responses until reaching a predetermined required number of times in a combination of the stimulation site and the recording site. In addition, the anti response management unit 81 transmits the remaining required number of times in the combination to the stimulation control unit 51, and the stimulation control unit 51 executes light stimulation by giving priority to a combination in which the remaining required number of times is larger.

In addition, in a case where anti response acquisition in a predetermined required number of times is completed in all combinations of the stimulation sites and the recording sites, the anti response management unit 81 detects a spike that is observed in anti responses of the respective combinations with good reproducibility, and sets the spike as an anti candidate spike. The anti response management unit 81 determines an anti candidate spike loss determination standard on the basis of a variation of the anti responses, and transmits the standard to the collision response management unit 82. In addition, the anti response management unit 81 transmits a four-channel waveform of the anti candidate spike to the priority control unit 54, and the four-channel waveform is used in initial vale setting in the priority control. The priority control in the priority control unit 54 will be briefly described with reference to FIG. 6 and FIG. 7.

Figure 6:
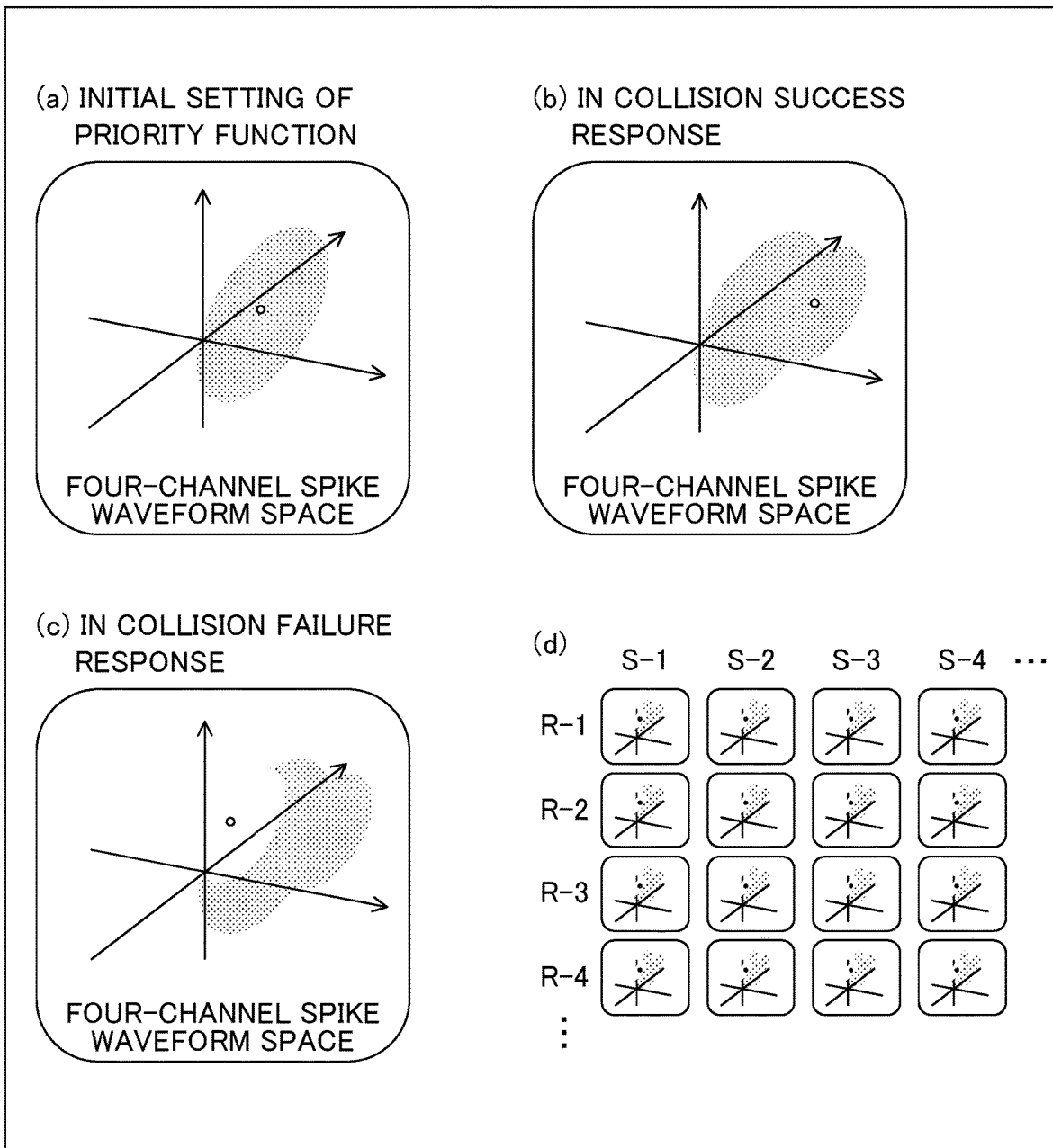
FIG. 6 is a diagram illustrating an example of priority control of efficiently acquiring collision success response.

FIG. 6 is a diagram illustrating an example of the priority control of efficiently acquiring a collision success response. For example, FIG. 6 is a diagram illustrating the priority control relating to anti candidate spikes detected in an anti response in a combination of a stimulation site and a recording site in a four-channel spike waveform space. In FIG. 6(*a*), a point indicated by a white circle represents a four-channel waveform of the anti candidate spike. In a case where a spontaneous spike of which the four-channel waveform resembles the anti candidate spike occurs, there is a high possibility that the spontaneous spike occurs from the same neuron. Accordingly, when light stimulation is executed in advance by setting the spontaneous spike as a target, there is a high possibility that a collision success response is obtained. Since the four-channel waveform that resembles the anti candidate spike is set as the target spike, the priority of the periphery of the four-channel waveform of the anti candidate spike is raised (gray region). A priority function (gray region) on the four-channel waveform space is calculated with respect to all anti candidate spikes, and is transmitted to the stimulation control unit 51. The stimulation control unit 51 detects spontaneous spikes at all of the recording sites R-1 to R-L on the basis of the priority function received from the priority control unit 54, and in a case where another spontaneous spike does not exist in a constant period at an arbitrary recording site and in a case where an anti candidate spike in which a waveform has certain priority or higher exists, a stimulation site at which the anti candidate spike is caused to occur is stimulated. The acquisition unit 52 acquires cell record information before and after the stimulation at all of the recording sites R-1 to R-L, stores the cell record information in the cell record information DB 300, and transmits the cell record information to the collision response management unit 82. The collision response management unit 82 determines whether the cell record information obtained at all of the recording sites R-1 to R-L is the collision success response (the lower drawing in FIG. 4(*b*)), the collision failure response (the lower drawing in FIG. 4(*c*)), or another response on the basis of the loss determination standard of the anti candidate spike. In addition, a four-channel waveform of the spontaneous spike of the cell record information determined as the collision success response and the collision failure response is transmitted to the priority control unit 54. FIG. 6(*b*) is a diagram illustrating priority control in the case of being determined as the collision success response. A white circle represents the four-channel waveform of the spontaneous spike when being determined as the collision success response. Since the determination is made as the collision success response, when another spike having a waveform that resembles the spontaneous spike occurs, light stimulation is performed by setting the spike as a target, and thus there is a high possibility that the collision success response is obtained. Accordingly, the priority of the periphery of the spontaneous spike waveform is raised (addition of the gray region). FIG. 6(*c*) is a diagram illustrating priority control in the case of being determined as the collision failure response. A white circle represents the four-channel waveform of the spontaneous spike when being determined as the collision failure response. Since the determination is made as the collision failure response, when another spike having a waveform that resembles the spontaneous spike occurs, even when light stimulation is performed by setting the spike as a target, there is a high possibility that the collision failure response is obtained. Accordingly, the priority of the periphery of the spontaneous spike waveform is lowered (reduction of the gray region). A priority function update result is transmitted to the stimulation control unit 51, and a stimulation site at which light stimulation is performed and a timing thereof are determined on the basis of the priority function.

FIG. 6(*d*) is a diagram illustrating an example of a drawing for efficiently obtaining the collision success response, and is a diagram illustrating an example in which the priority is controlled in parallel, and a target spike is retrieved in real time.

FIG. 6(*d*) illustrates an example in which the priority function is processed in parallel with respect to a detected anti candidate spike in all combination of the recording sites R-1 to R-L and the stimulation sites S-1 to S-K. In this embodiment, the projection target identification device 3 can acquire the cell record information in parallel from a plurality of recording sites, and thus it is possible to execute calculation of the priority in parallel in real time. Accordingly, the projection target identification device 3 can retrieve a plurality of target spikes of a plurality of neurons in real time.

Figure 7:
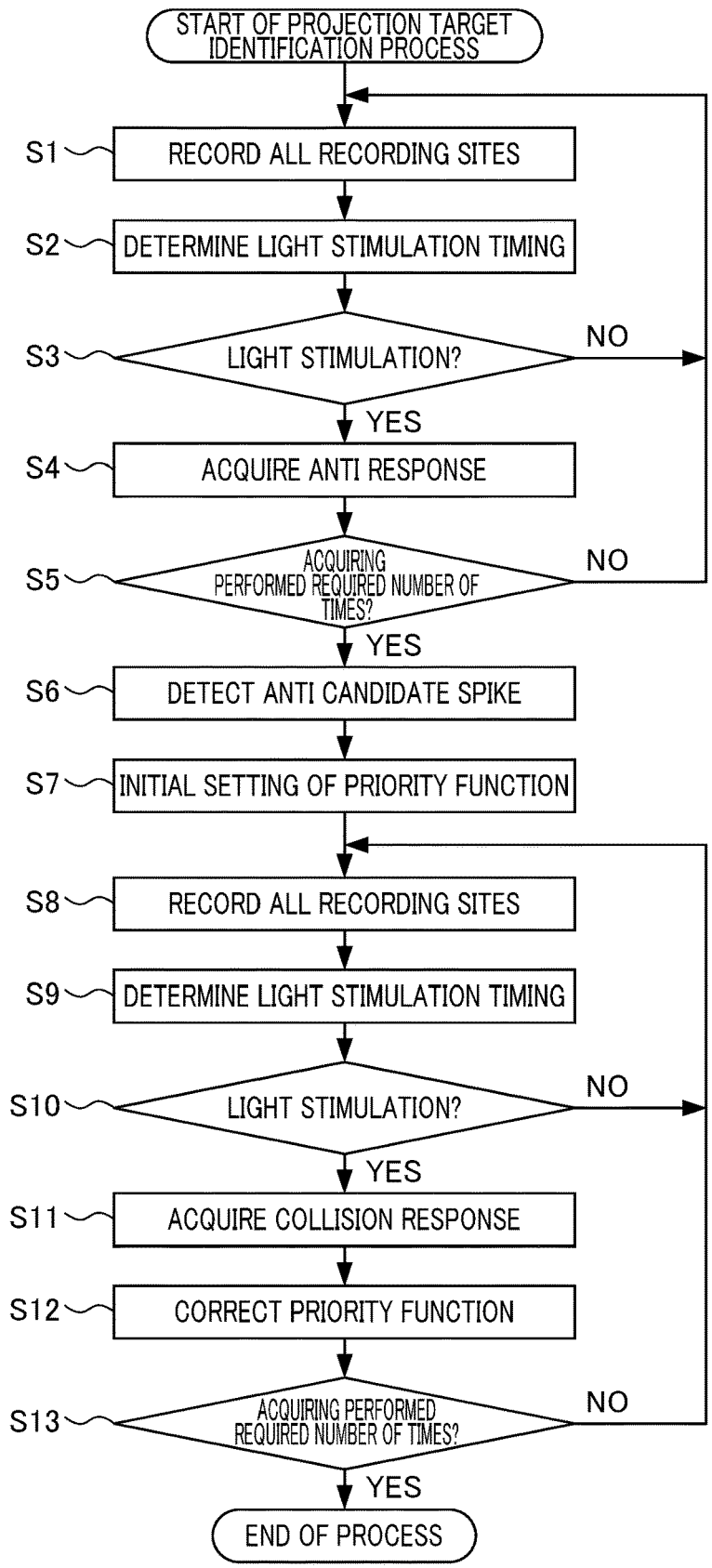
FIG. 7 is a flowchart illustrating a flow of a projection target identification process executed by the projection target identification device illustrated in FIG. 2.

FIG. 7 is a flowchart illustrating a flow of a projection target identification process executed by the projection target identification device 3 illustrated in FIG. 2.

In step S1, the acquisition unit 52 stores cell record information for a constant period in the past while acquiring and updating cell record information of all of the recording sites for every time, and transmits the cell record information to the stimulation control unit 51.

In step S2, the stimulation control unit 51 determines irradiation timing of light stimulation that is applied to K pieces (K is an integral value of two or greater) of projection target candidates on the basis of a predetermined system.

In step S3, the stimulation control unit 51 determines whether or not light stimulation is applied. In a case where the light stimulation is not applied, in step S3, the determination is made as "NO", and the process is returned to step S1. In contrast, in a case where the light stimulation is applied, in step S3, the determination is made as "YES", and the process proceeds to step S4. In addition, in step S4, the anti response management unit 81 acquires and manages information relating to the anti response as anti response information.

In step S5, the anti response management unit 81 determines whether or not the number of anti responses acquired reaches a predetermined required number of times. In a case where the required number of times is not reached, in step S5, the determination is made as "NO", and the process is returned to step S1. In contrast, in a case where the required number of times is reached, in step S5, the determination is made as "YES", and the process proceeds to step S6. In addition, in step S6, the anti response management unit 81 performs setting a determination standard of detection and disappearance of the anti candidate spike, and transmits predetermined information to the collision response management unit 82 and the priority control unit 54.

In step S7, the priority control unit 54 performs initial setting of the priority function on the basis of a waveform of the anti candidate spike, and transmits information thereof to the stimulation control unit 51.

In step S8, the acquisition unit 52 stores cell record information for a constant period in the past while acquiring and updating cell record information of all of the recording sites for every time, and transmits the cell record information to the stimulation control unit 51.

In step S9, the stimulation control unit 51 detects the spontaneous spike on the basis of the cell record information of all of the recording sites, and determines a light stimulation timing in accordance with the priority function.

In step S10, the stimulation control unit 51 determines whether or not light stimulation is applied. In a case where the light stimulation is applied, in step S10, the determination is made as "NO", and the process is returned to step S8. In contrast, in a case where the light stimulation is applied, in step S10, the determination is made as "YES", and the process proceeds to step S11. In addition, in step S11, the collision response management unit 82 determines whether the collision response is collision success or collision failure. The collision response management unit 82 manages a waveform of the spontaneous spike of the collision response as collision response information, and transmits the collision response waveform to the priority control unit 54.

In step S12, the priority control unit 54 corrects the priority function in accordance with the collision success or the collision failure.

In step S13, the collision response management unit 82 determines whether or not the number of acquisition times of the collision success response reaches a predetermined required number of times. In a case where the predetermined required number of times is not reached, in step S13, the determination is made as "NO", and the process is returned to step S8. In contrast, in a case where the predetermined required number of times is reached, in step S13, the determination is made as "NO", and the process is terminated as is.

Hereinbefore, an embodiment of the invention has been described. However, the invention is not limited to the above-described embodiment, and it should be understood that changes, modifications, and the like are included in the scope capable of accomplishing the object of the invention.

Note that, the series of processes (for example, the projection target identification process) employed in the above-described embodiment includes the following two stages, and may be provided with various functions. That is, Stage 1 is a process relating to efficient acquisition of the anti responses. According to this, it is possible to acquire responses of a plurality of recording sites per light stimulation performed once. In addition, Stage 2 is a process relating to efficient acquisition of the collision success responses. According to this, it is possible to execute the priority control of the target spike in a spike waveform space (for example, a four-channel waveform space). According to this, it is possible to process the stimulation sites and the recording sites in parallel in real time. According to this, it is possible to efficiently retrieve the target spike. In addition, in summary, the series of processes (for example, the projection target identification process) employed in the above-described embodiment can be provided with the following functions.

(1) A multi-point light stimulation candidate is prepared, and a range of light stimulation performed once can be limited.

(2) It is possible to obtain valid data at a plurality of recording sites as many as possible with the light stimulation performed once.

(3) It is possible to efficiently calculate a spike for collision identification from a plurality of recording sites.

(4) It is possible to perform automatic control with respect to combinations of a plurality of light stimulation sites and a plurality of recording sites simultaneously and in parallel. According to this, it is possible to realize simultaneous identification of spike signals which are transmitted between a plurality of brain areas.

In addition, for example, in the above-described embodiment, description has been given of the case of using an electrode that is inserted in the brain. However, for example, responses of the recording sites may be optically acquired by microscope imaging using a potential-sensitive fluorescent molecule without using the electrode.

In addition, for example, in the above-described embodiment, as the gene-modified animal, description has been made by using a rat in which ChR2 is exhibited at the entirety of the brain, but there is no particular limitation thereto. That is, as the animal that is used, other animals such as a mouse and a marmoset may be used. In addition, a gene (or protein) set as a target is not limited to ChR2, and an arbitrary gene (or protein) may be set as the target as long as the object of the invention can be accomplished.

In addition, for example, in the above-described embodiment, description has been given of a case where the priority control unit 54 corrects and determines the priority, but there is no particular limitation to this. That is, the priority control unit 54 may not correct the priority and may not add a change to the original priority.

In addition, for example, in the above-described embodiment, description has been given of an example in which the priority that is controlled is set as the order of execution of the light stimulation, but there is no particular limitation thereto. That is, other items such as an execution range or an execution time of the light stimulation may be controlled as the priority.

In addition, for example, the above-described series of processes may be executed by hardware or software. In other words, the functional configuration illustrated in FIG. 3 is illustrative only, and there is no particular limitation thereto. That is, it is sufficient if the information processing system is provided with a function capable of executing the above-described series of processes as a whole, and use of any block for realizing the function is not limited to the example illustrated in FIG. 2. In addition, a location at which the functional block exists is not particularly limited to FIG. 3, and may be an arbitrary location. In addition, one functional block may be constituted by hardware alone, software alone, or a combination thereof.

In addition, for example, in a case where the series of processes is executed by software, a program that constitutes the software is installed in a computer or the like over a network or from a recording medium. The computer may be a computer provided with dedicated hardware. In addition, the computer may be a computer capable of executing various functions by installing various programs, for example, a general-purpose smart phone or a pc other than a server.

In addition, for example, a recording medium including the program is constituted by a removable medium (not illustrated) that is distributed separately from a device main body to provide a program to a user, a recording medium that is provided to the user in a state of being provided in the device main body in advance, or the like.

Note that, in this specification, it should be understood that steps for describing the program recorded in the recording medium includes not only processes performed in time series according to a procedure but also processes executed in parallel or individually even though the processes are not processed in time series. In addition, in this specification, it is assumed that the term of the system represents an overall apparatus that is constituted by a plurality of devices, a plurality of units, and the like.

In other words, the projection target identification device to which the invention is applied may employ various embodiments including the following configurations. That is, the projection target identification device to which the invention is applied may be a neuron projection target identification device that identifies one or more projection targets among K pieces (K is an integral value of two or greater) of projection target candidates (for example, the stimulation sites S-1 to S-K in FIG. 4) with respect to predetermined projection source cells (for example, recording cells N1 to N3 in FIG. 4). The projection target identification device includes:

a spike signal acquisition unit that records spike signals of a plurality of neurons at L pieces (L is an integral value of two or greater) of recording sites (R-1 to R-L) on the basis of a predetermined system;

a stimulation timing determination unit that determines an efficient timing of applying stimulation to the projection target candidates on the basis of spike signal information;

a projection target determination unit (for example, the anti response management unit 81 or the collision response management unit 82 in FIG. 3) that determines whether or not the projection target candidates are real projection targets on the basis of the spike signal information within a predetermined period of time before or after the stimulation when the stimulation is applied to the projection target candidates; and a priority control unit (for example, the priority control unit 54 in FIG. 3) that corrects a method of the stimulation timing determination on the basis of a determination result of the projection target determination unit and the spike signal information.

According to this, after identifying a plurality of routes between a plurality of brain areas, it is possible to acquire spike signals which are transmitted through the routes.

In addition, specifically, the priority control unit of the projection target identification device to which the invention is applied can execute control in a t (t is an arbitrary integral value of one or greater)-channel waveform space.

According to this, more accurate cell identification becomes possible, and the neuron projection target can be more efficiently clarified.

According to this, it is possible to efficiently identify spike signals and it is possible to clarify the neuron projection target by appropriately using an existing technology.

In addition, specifically, the priority control unit of the projection target identification device to which the invention is applied may control the priority by a priority function in M (M is an arbitrary integral value of one or greater)-channel spike waveform space.

In addition, the N-channel spike waveform space may be a four-channel spike waveform space.

EXPLANATION OF REFERENCE NUMERALS

1 . . . MULTI-CELL RECORDING DEVICE, 2 . . . MULTI-POINT LIGHT STIMULATION DEVICE, 3 . . . PROJECTION TARGET IDENTIFICATION DEVICE, 21 . . . CPU, 51 . . . STIMULATION CONTROL UNIT, 52 . . . ACQUISITION UNIT, 53 . . . MANAGEMENT UNIT, 54 . . . PRIORITY CONTROL UNIT, 55 . . . OUTPUT INFORMATION GENERATION UNIT, 81 . . . ANTI RESPONSE MANAGEMENT UNIT 82 . . . COLLISION RESPONSE MANAGEMENT UNIT, 300 . . . CELL RECORD INFORMATION DB, S-1 TO S-K . . . STIMULATION SITE, R-1 TO R-L . . . RECORDING SITE

The invention claimed is:

1. A neuron projection target identification method that identifies one or more projection targets among K pieces (K is an integral value of two or greater) of projection target candidates with respect to predetermined projection source cells among a plurality of projection source cell candidates, comprising:

a spike signal acquisition step of recording spike signals of a plurality of neurons at L pieces (L is an integral value of two or greater) of recording sites (R-1 to R-L) on the basis of a predetermined system;

a projection destination stimulation step of stimulating each of the K pieces of projection target candidates as a stimulation target at a predetermined timing;

a stimulation timing determination step of determining the priority for determining whether the detected spike signal applies to each projection source cell candidate, and determines whether or not to execute a stimulation for determining whether or not the projection source cell is a true projection target at the timing when the spike signal of the predetermined projection source cell candidate is detected, on the basis of spike signal information of the plurality of projection source cell candidates induced by stimulation to a predetermined projection target;

a projection target determination step of determining whether or not the projection target candidates are projection targets on the basis of the spike signal information for predetermined projection source cells within a predetermined period of time before or after the stimulation when the stimulation is applied to each of one or more stimulation targets; and a priority control step of correcting the priority given to each of the plurality of projection source cell candidates on the basis of a determination result of the projection target determination unit and the spike signal information used to determine the projection target determination unit.

2. The neuron projection target identification method according to claim 1, wherein the priority control step controls priority by a priority function in M (M is an arbitrary integral value of one or greater)-channel spike waveform space.

3. The neuron projection target identification method according to claim 2, wherein the M-channel spike waveform space is a four-channel spike waveform space.

* * * * *